United States Patent [19]
House

[11] Patent Number: 5,238,009
[45] Date of Patent: Aug. 24, 1993

[54] SELF-CATHERIZATION AID

[76] Inventor: Jamie G. House, 5220 Sorrento, Boise, Id. 83704

[21] Appl. No.: 713,720

[22] Filed: Jun. 11, 1991

[51] Int. Cl.⁵ .............................................. A61F 5/451
[52] U.S. Cl. .................................. 128/883; 128/842; 128/845
[58] Field of Search .................. 128/79, DIG. 25, 157, 128/160, 842, 845, 846, 869, 883; 604/116, 349–353; 141/337, 338, 392

[56] References Cited

U.S. PATENT DOCUMENTS

| | | | |
|---|---|---|---|
| 2,605,582 | 8/1952 | Allen | 141/337 X |
| 3,203,420 | 8/1965 | Lockhart | 604/353 |
| 3,300,786 | 1/1967 | Rosenvold et al. | 128/858 X |
| 3,804,134 | 4/1974 | Wehking | 141/337 X |
| 3,939,827 | 2/1976 | Brunstetter | 128/79 |
| 4,568,340 | 2/1986 | Giacalone | 604/353 |
| 4,588,397 | 5/1986 | Giacalone | 604/349 |
| 4,590,931 | 5/1986 | Kidwell, Jr. | 128/162 |
| 4,896,707 | 1/1990 | Cowles | 141/337 |
| 4,971,074 | 11/1990 | Hrubetz | 128/79 X |
| 5,078,189 | 1/1992 | Rosonet | 141/337 |

FOREIGN PATENT DOCUMENTS

| | | | |
|---|---|---|---|
| 520557 | 3/1931 | Fed. Rep. of Germany | 128/79 |
| 1508356 | 1/1968 | France | 604/351 |
| 2221116 | 10/1974 | France | 128/79 |
| 154651 | 10/1932 | Switzerland | 128/79 |

Primary Examiner—Robert A. Hafer
Assistant Examiner—Sam Rimell
Attorney, Agent, or Firm—Klarquist, Sparkman, Campbell, Leigh & Whinston

[57] ABSTRACT

A self-catheterization aid for use by male patients having impaired wrist, hand and finger movement due to traumatic spinal cord injury or neuromuscular diseases. The self-catheterization aid comprises a strip of flexible material having an arcuate semi-annular shape. The patient fits the device around his penis to form a circumferential tubular support platform that stabilizes the penis to allow for self-catheterization with either an indwelling catheter or an intermittent internal catheter. The device is easily manipulated by patients having impaired hand and wrist movement.

6 Claims, 2 Drawing Sheets

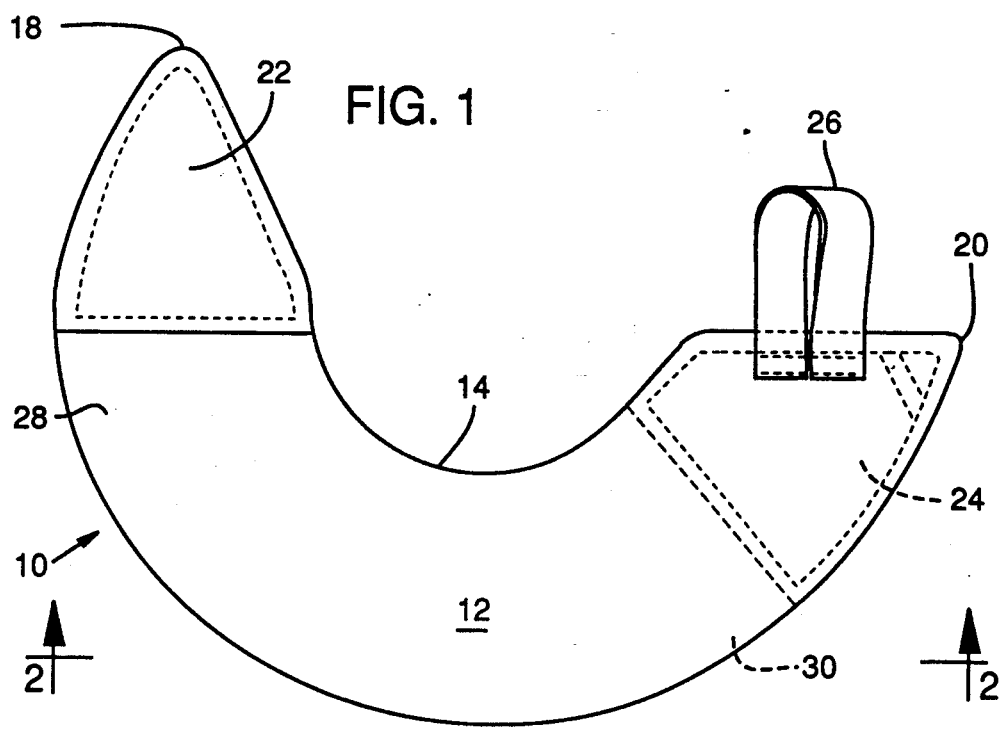
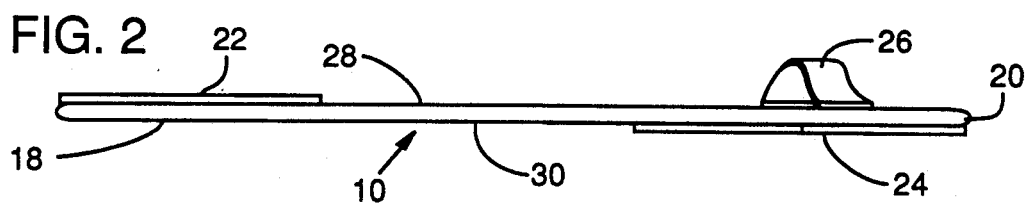
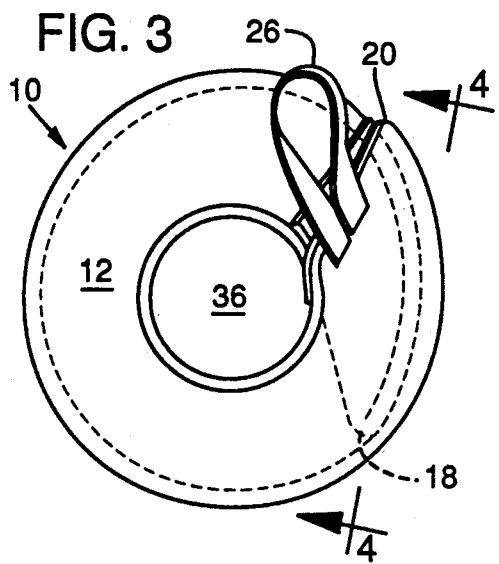
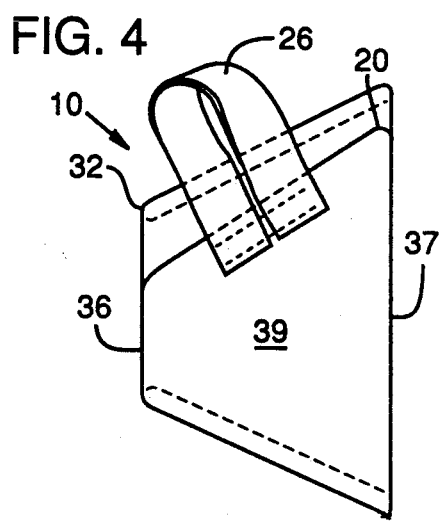

SELF-CATHERIZATION AID

TECHNICAL FIELD

This invention relates to devices utilized by disabled males as an aid to self-catheterization with an internal catheter to facilitate urine evacuation.

BACKGROUND OF THE INVENTION

Traumatic spinal cord injury and neuromuscular diseases often result in severely impaired movement of the extremities. Impaired wrist, hand and finger movement are common with spinal cord injuries and neuromuscular diseases, especially traumatic spinal cord injury to the higher cervical spinal cord segments. Impaired coordination is a secondary problem often associated with these injuries. In addition to impaired movement of the extremities, spinal cord injuries and neuromuscular diseases often cause impaired bladder function. Not only may it be difficult to adequately empty the bladder, resulting in the need to routinely augment bladder drainage by intermittent self-catheterization with an internal catheter, but bladder control is also often compromised, resulting in unintentional discharge of urine. Elderly patients sometimes experience the same kinds of bladder control problems.

Various kinds of catheters have been used to solve the problems associated with incontinence caused by traumatic spinal cord injury, neuromuscular diseases, and advanced age. For example, there are generally three types of catheters used with male patients: External catheters (also known as condom catheters); indwelling internal catheters that are intended to remain inserted into the patient's bladder for extended periods; and intermittent internal catheters that are inserted only when catheterization is necessary.

The specific kind of catheter used at any given time varies, and depends to some extent upon the specific nature of the patient's requirements. For example, an external catheter is generally used on an ongoing basis when the patient's bladder has regained some degree of muscle control following a traumatic injury to the spinal cord. These devices fit externally over the penis, and usually have some kind of a sealing ring at the base of the penis. They are generally the most convenient and trouble free for use on an extended basis. However, external catheters can not always be used. For example, in the period immediately after a traumatic spinal cord injury the bladder is incapable of even spontaneous contraction which would cause urine to void. Since bladder contraction is a necessary requisite to use of an external catheter, use of these devices during the time period when the bladder does not function would be inappropriate. Furthermore, even when these devices may be used, there is still a need to utilize internal catheterization devices since there are times when an external catheter would be inconvenient or impossible to utilize. An external catheter is described by U.S. Pat. No. 4,588,397 to Giacalone.

An internal catheter is a small tubular device that is inserted into the urethra and extends up the urethra and into the bladder, thereby facilitating complete drainage of urine from the bladder. These devices may be used even when the bladder is incapable of spontaneous contraction. Indwelling internal catheters are generally used when the patient's bladder is incapable of even spontaneous contraction, such as the first few weeks immediately following a traumatic spinal cord injury. However, use of indwelling internal catheters over a long period of time is not possible because they are often associated with bacterial infections.

Due to the problems associated with indwelling internal catheters, patients are changed to intermittent internal catheterization as soon as their health is stabilized following a traumatic injury to the spinal cord. This eliminates the risk of infection associated with indwelling catheters. Intermittent internal catheterization is performed only when it is necessary to evacuate urine from the bladder (generally every four to six hours). Thus, these catheters may be used by patients who remain institutionalized and have not converted to use of external catheters. In addition, intermittent internal catheters may be utilized by those individuals who use external catheters to augment bladder drainage. For example, intermittant internal catheters may be used at those times when it would be inconvenient to use an external catheter, such as in the morning before showering, or at times when it would not be possible to empty the leg bag that is associated with an external catheter.

However, because patients suffering from traumatic spinal cord injury or various neuromuscular diseases have severely impaired movement of their hands and fingers, self-catheterization with either an internal intermittant or external catheter can be an extremely difficult or impossible procedure. As a result, many patients are unable to perform self-catheterization as a method of evacuating urine. This results in the procedure being performed by someone else, with the resultant deprivation of independence and privacy.

Thus, a need exists for a device that enables male patients suffering from injury or disease which causes incontinence and limited movement of the lower extremities, to perform self-catheterization. This is the primary objective of the present invention.

SUMMARY OF THE INVENTION

The present invention is a strip of flexible but laterally stiff or semi-rigid material such as fabric-backed foam rubber or foam rubber. In its preferred form, the strip has an arcuate semi-annular shape. The strip has two laterally spaced apart opposite ends, and each end includes a fastening device so that the ends may be adjustably fastened together. The strip normally lies flat when the ends of the strip are not connected. When the ends of the strip are connected the device forms a hollow frustum axially stiff tube having a frusto-conical shape in the preferred form. The tube has a large circular opening at the base of the frustum and a relatively smaller circular opening at the apex of the frustum. Because of the adjustable nature of the end fasteners, the diameters of the openings are adjustable.

In use, the device is fitted around the penis to form a circumferential tubular platform that stabilizes the penis to allow for self-catheterization. The patient places the strip with the ends unfastened under his penis, then draws the opposite ends over the penis and fastens them together to form the tubular shape. A hook or strap is provided as a handle at one end of the strip to facilitate the fastening of the two ends together. The opening at the base end of the tube rests against the patient's lower abdomen and groin area around the base of the penis. The opening at the apex of the tube encircles and engages the glans of the patient's penis. When the device is fastened around the penis, the penis is stabilized and supported by the resulting relatively rigid tube so that the patient may insert a catheter into his urethra.

With this device a male patient with impaired use of his hands and fingers is able to independently and privately perform self-catheterization with either an intermittent or indwelling internal catheter.

BRIEF DESCRIPTION OF THE DRAWINGS

FIG. 1 is a plan view of a preferred embodiment of the present invention in the open position.

FIG. 2 is a side view of the device in its open position.

FIG. 3 is a plan view of the device with its two ends fastened together.

FIG. 4 is a sectional view taken along the line 4—4 of FIG. 3.

DETAILED DESCRIPTION OF THE INVENTION

Figure 5:
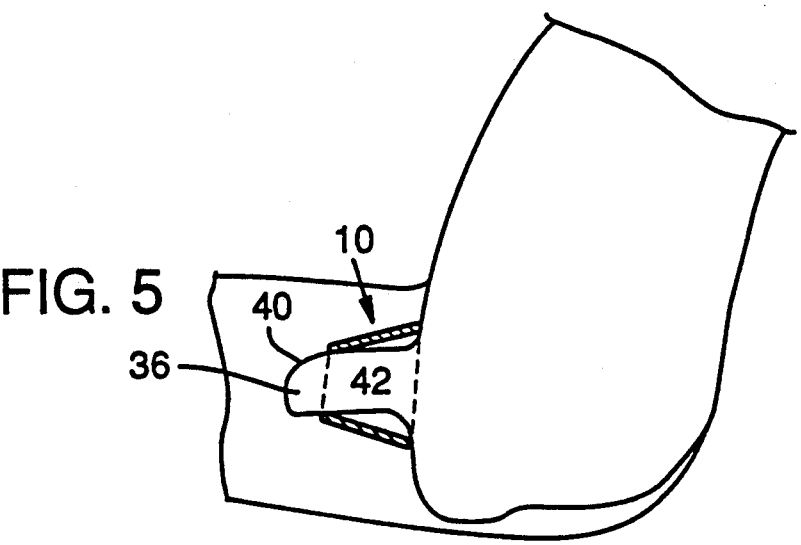
FIG. 5 is a schematic view of a male patient with the device fastened around the penis.

A preferred embodiment of the self-catheterization aid 10 manufactured in accordance with the present invention is depicted in FIG. 1. The self-catheterization aid 10 comprises a semi-annular arcuate strip 12. The strip 12 is flexible, and it lies generally flat when not flexed in use. It is preferably made of a material such as fabric-backed foam rubber. Standard foam rubber without the fabric-backing would also suffice. In any event, closed cell foam rubber is preferred since it would not absorb moisture and is comfortable to the patient. Any other flexible or semi-rigid materials would suffice as a material for strip 12.

Strip 12 is formed in a one piece semi-annular arcuate shape that includes a concave inner edge 14, a convex outer edge 16, and two laterally spaced apart opposite generally pointed ends 18 and 20. Both inner edge 14 and outer edge 16 are rounded between the broad inner and outer surfaces of the strip so the device is more comfortable for the user. Ends 18 and 20 have fastening strips 22 and 24 attached thereto. Fastening strips 22 and 24 are preferably Velcro ®. In that case fastening strip 22 would be the 37 eye" portion of the Velcro ®, and fastening strip 24 would be the "hook" portion of the Velcro ®. Other fastening systems such as a standard snap type device would suffice, but Velcro ® is preferred because it is very easy for a patient having impaired hand and finger movement to fasten and unfasten. Velcro ®-type fasteners also provide infinite adjustability. Fastening strip 22 (the eye portion) is attached to the upper side 28 of strip 12 on end 18. Fastening strip 24 (the hook portion) is attached to the lower side 30 of strip 12 on end 20. Both fastening strips 22 and 24 are attached to strip 12 by stitching the fastening strip to the foam rubber. Other conventional means of attachment, such as glue, would suffice.

Strip 12 also includes a handle 26 to provided the user a convenient and easily accessible handhold. Handle 26 is preferably a flexible cloth material, such as a ⅜ inch wide nylon strap, formed into a loop and stitched into the upper side 28 of strip 12. Other flexible strapping material or handle type devices would suffice.

In use, ends 18 and 20 are coupled together by joining them together and fastening them with fastening strips 22 and 24. As noted, fastening strip 22 is attached to the upper side 28 of strip 12 on end 18. Fastening strip 24 is attached to the lower side 30 of strip 12 on end 20. Thus, to fasten the two ends 18 and 20 together, end 20 is laid over end 18 such that the fastening strips 22 and 24 overlap each other. When the fastening strips are in this position the ends 18 and 20 are pressed together to fasten the Velcro ®.

The self-catheterization aid 10 generally describes a hollow frustum when ends 18 and 20 are fastened (FIGS. 3 and 4). When ends 18 and 20 are fastened together an opening 36 is formed at the apex end 32 of the frustum, and a relatively larger opening 37 is formed at the base end 34 of the frustum. A central passageway 39, which is generally frusto-conical in shape, larger at the base and relatively smaller at the apex, runs through the length of the frustum. Varying the distance that end 20 overlaps end 18 varies the diameter of the openings 36 and 37. The diameter of openings 36 and 37 can be increased by decreasing the distance that end 20 overlaps end 18. Similarly, the diameter of openings 36 and 37 may be decreased by increasing the distance that end 20 overlaps end 18. When a Velcro ®-type fastening system is utilized the amount of overlap of fastening strips 22 and 24 is infinitely adjustable within the lengths of the respective strips.

Use of the self-catheterization aid 10 is depicted schematically in FIG. 5. Without the aid of the present invention it would be extremely difficult or impossible for a patient having impaired hand and finger movement to insert an internal catheter into the urethra because the penis 36 is unsupported and flexible. However, as seen in FIG. 5, the self-catheterization device 10, when applied to the penis 36 such that it forms a frusto-conical circumferential support platform for the penis, enables the patient perform self-catheterization by inserting an internal catheter into the urethra. The device stabilizes the patient's penis so that self-catheterization is a relatively easy procedure, even for patient's with severely impaired hand and finger movement.

To apply the self-catheterization aid 10 of the present invention to the penis 36, the patient places the open, uncoupled device (FIG. 1) under the penis 36 such that the ends 18 and 20 are directed away from the patient's body. Thus, the outer convex edge 16 rests against the patient's groin area below the penis 36. The patient grasps handle 26 in one hand and end 18 in the other, and draws the ends together over and around the penis. Ends 18 and 20 are drawn together until the self-catheterization aid 10 completely encircles the penis, at which time end 20 is pressed onto end 18 to couple fastening strips 22 and 24. When ends 18 and 20 are fastened together, base end 34 of the device rests against the patient's abdomen and groin area around the base 38 of the penis 36. The fastened device therefore forms a frusto-conically shaped tubular support platform that completely encircles the patient's penis. The glans 40 of the patient's penis 36 extends through opening 36 at the apex end 32 of the assembled self-catheterization aid 10 to provide the patient easy access to his urethra.

The size of opening 36 is adjusted by the patient so that it is substantially the same diameter as the patient's penis 36, and thus supports and engages the penis. The shaft 42 of the patient's penis 36 extends through central passageway 39, and the glans 40 is held generally external to the apex end 32 of the assembled device. Because base end 34 has a larger opening 37 than the opening 36 at apex end 32, and because base end 34 rests against the patient's abdomen and groin area around the base 38 of the penis 36, the patient's penis is supported and stabilized to limit movement in any direction. This greatly facilitates self-catheterization.

Once applied to the patient as seen in FIG. 5, the patient may insert an internal catheter into his urethra and bladder to evacuate urine from his bladder. The self-catheterization aid 10 of the present invention may be used equally well with intermittent internal catheters, and indwelling catheters. When an intermittent internal catheter is used, the catheter is removed from the urethra once bladder drainage is complete, and the self-catheterization aid 10 is unfastened and removed from the patient's penis 36. It has been found that the self-catheterization aid 10 of the present invention may also be used to facilitate self-application of a condom catheter.

ALTERNATIVE EMBODIMENT

Figure 6:
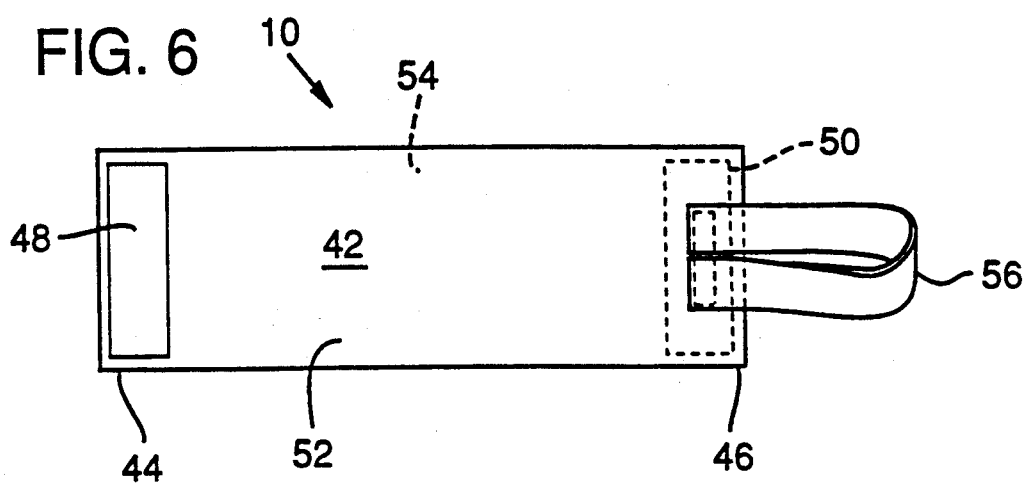
FIG. 6 is a plan view of an alternative embodiment of the present invention in the open position.

An alternative embodiment of the self-catheterization aid 10 of the present invention is depicted in FIG. 6. In this embodiment the strip 42 comprises a substantially rectangular strip having opposite ends 44 and 46. As with the preferred embodiment, the embodiment depicted in FIG. 6 is preferably made of a flexible material such as fabric-backed foam rubber.

Strip 42 lies flat when not flexed in use. The "eye" portion 48 of the Velcro ® fastening strip is attached to top side 52 of strip 42 at end 44. The "hook" portion 50 of the Velcro ®fastening strip is attached to the bottom side 54 of strip 42 at end 46. A loop of fabric as a handle 56 is stitched to the top side 52 of strip 42 at end 46.

When ends 44 and 46 are fastened together (FIG. 7), the device forms a cylinder having a base end 58 and a distal end 60. The cylinder has a first opening 62 at base end 58, a second opening 64 at distal end 60, and a central passageway 66 therebetween.

As with the preferred embodiment, the diameter of first opening 62 and second opening 64, and also central passageway 66 are adjustable and may be increased or decreased by varying the amount of overlap of end 46 on end 44. In use, the diameter of the cylinder is adjusted by the user to coincide substantially with the diameter of the penis 36. Thus, in use the assembled device forms a cylindrical tube for supporting the patient's penis.

Figure 7:
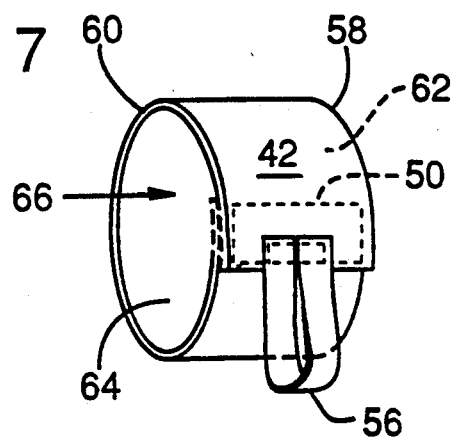
FIG. 7 is a perspective view of the embodiment of FIG. 6 with its two ends fastened together.

Application of the embodiment shown in FIGS. 6 and 7 is similar to that described above for the preferred embodiment. The patient places the open strip (FIG. 6) beneath the underside of the penis such that the long-axis of the rectangular strip is generally perpendicular to the longitudinal axis of the patient's penis. The device is wrapped around the penis by grasping the handle 56 in one hand and end 44 in the other, then drawing the two ends 44 and 46 over and around the penis. The ends are then fastened together by overlapping the two parts of the Velcro ® fastening strip and pressing them together.

While the present invention has been described in accordance with preferred embodiments, it is to be understood that certain substitutions and alterations may be made thereto without departing from the spirit and scope of the appended claims.

I claim:

1. A self-catheterization aid comprising:
   a flexible strip member having opposite ends, a length sufficient to encircle the penis of the user and overlap the opposite ends, and a width sufficient to extend from the base of the penis to the glans of the penis when the strip encircles the penis;
   fastening means on the strip for fastening the overlapping opposite ends together when the strip encircles the penis, the strip with the ends overlapping and fastened together defining a semi-rigid tubular support platform for supporting the penis during catheterization when the strip encircles the penis, with one end opening of the tubular platform positioned at the base of the penis and the other end opening behind the glans of the penis;
   a handhold attached to and extending from one end of said strip member for facilitating overlapping the opposite ends to fasten the opposite ends together, and for facilitating unfastening the opposite ends; and
   the strip lying substantially flat and having an arcuate shape when the opposite ends are unfastened.

2. A self-catheterization aid, comprising:
   penis support means comprising a flexible strip having an inner edge and an outer edge, and two laterally spaced apart opposite ends, the strip lying substantially flat in an unflexed first position, the strip having an opposed pair of parallel side edges in the first position;
   a handhold attached to and extending from one end of said strip member for facilitating overlapping the opposite ends and for facilitating removing the overlapped opposite ends from the overlapped position; and
   planar fastening means for coupling the two ends when overlapped, and for securing the apparatus in a second position for supporting the penis, the length of the strip being sufficient to encircle the penis of the user and overlap the ends, and the width of the strip sufficient to extend substantially from the base of the penis to the glans of the penis when the strip encircles the penis.

3. A method of self-catheterization using an internal catheter comprising the steps:
   providing a flexible strip member that lies substantially flat when in an unflexed conditions but that can be flexed to form a generally tubular or frusto-conical self-supported shape by joining opposite end portions of the strip;
   sizing the strip member such that it has a length sufficient to encircle the penis of the user with the opposite ends of the strip overlapping one another, and width sufficient to extend from the base of the penis to the glans of the penis with the strip encircling the penis;
   encircling the penis with the strip member and overlapping the opposite ends such that an upper edge of the strip lies behind the glans of the penis and has an inside diameter smaller than the diameter of the glans and such that a lower edge of the strip member lies against the groin at the base of the penis and has an inside diameter at least as large as the base of the penis;
   while encircling the penis as described aforesaid, fastening the overlapped opposite ends together to form a semi-rigid self-supporting tubular support platform that supports the penis during catheterization thereof; and
   while supporting the penis as aforesaid, inserting an internal catheter into the urethra.

4. The method of claim 3 wherein the step of encircling the penis includes engaging a handle provided at least one end of the strip member to move said one end toward said opposite end.

5. The method of claim 3 wherein the step of fastening the overlapped ends of the strip member to form the tubular support platform of indicated diameters at its top and bottom edges is facilitated by providing adjustable pressure-responsive fastening means on abutting surfaces of the overlapped ends.

6. The method of claim 3 wherein the step of encircling includes forming the strip member into a generally frusto-conical shape such that the lower edge of the platform has a larger diameter than the upper edge thereof.

* * * * *